United States Patent
Wang et al.

(10) Patent No.: US 11,142,481 B2
(45) Date of Patent: Oct. 12, 2021

(54) ADDITIVE FOR INCREASING EARLY ACTIVITY INDEX OF NICKEL SLAG AND PREPARATION METHOD THEREOF

(71) Applicant: Beijing University of Technology, Beijing (CN)

(72) Inventors: Yali Wang, Beijing (CN); Jianfeng Wang, Beijing (CN); Yunfang Lv, Beijing (CN); Zhenguo Wang, Beijing (CN); Yuanzhong Han, Beijing (CN); Shichao Zhang, Beijing (CN)

(73) Assignee: BEIJING UNIVERSITY OF TECHNOLOGY, Beijing (CN)

( * ) Notice: Subject to any disclaimer, the term of this patent is extended or adjusted under 35 U.S.C. 154(b) by 0 days.

(21) Appl. No.: 16/814,262

(22) Filed: Mar. 10, 2020

(65) Prior Publication Data

US 2020/0361822 A1 Nov. 19, 2020

(30) Foreign Application Priority Data

May 17, 2019 (CN) .......................... 201910416728.5

(51) Int. Cl.
*C04B 24/00* (2006.01)
*C04B 7/147* (2006.01)
*C07C 213/06* (2006.01)

(52) U.S. Cl.
CPC ............ *C04B 24/005* (2013.01); *C04B 7/147* (2013.01); *C07C 213/06* (2013.01)

(58) Field of Classification Search
CPC ..... C04B 7/147; C04B 18/144; C04B 20/023; C04B 24/005; C04B 24/04; C04B 24/122; C07C 213/06; Y02W 30/91
See application file for complete search history.

(56) References Cited

FOREIGN PATENT DOCUMENTS

| CN | 100404456 C | * | 7/2008 | ......... C04B 40/0039 |
|---|---|---|---|---|
| CN | 108191286 A | * | 6/2018 | ........... C04B 103/52 |

* cited by examiner

*Primary Examiner* — Anthony J Green
(74) *Attorney, Agent, or Firm* — Collard & Roe, P.C.

(57) ABSTRACT

An additive for increasing an early activity index of nickel slag and a preparation method thereof, belonging to the field of additive technologies, are provided. The preparation method includes: successively adding maleic anhydride and triethanolamine to a reactor; setting the heating temperature to 50° C. for reaction, where a large amount of heat is released during the reaction; when the reaction temperature decreases to 60° C. after heat is released in the reaction, allowing triethanolamine maleate to react with a solution of bromine in carbon tetrachloride; adding water to the mixture, where the weight percentage content of the added water is 60%; separating and removing carbon tetrachloride from water; and conducting uniform stirring to obtain the additive. A molar ratio of the maleic anhydride, the triethanolamine, and bromine is (0.2-1):1:(0.2-1), and a molar ratio of the maleic anhydride to the bromine is 1:1.

4 Claims, 1 Drawing Sheet

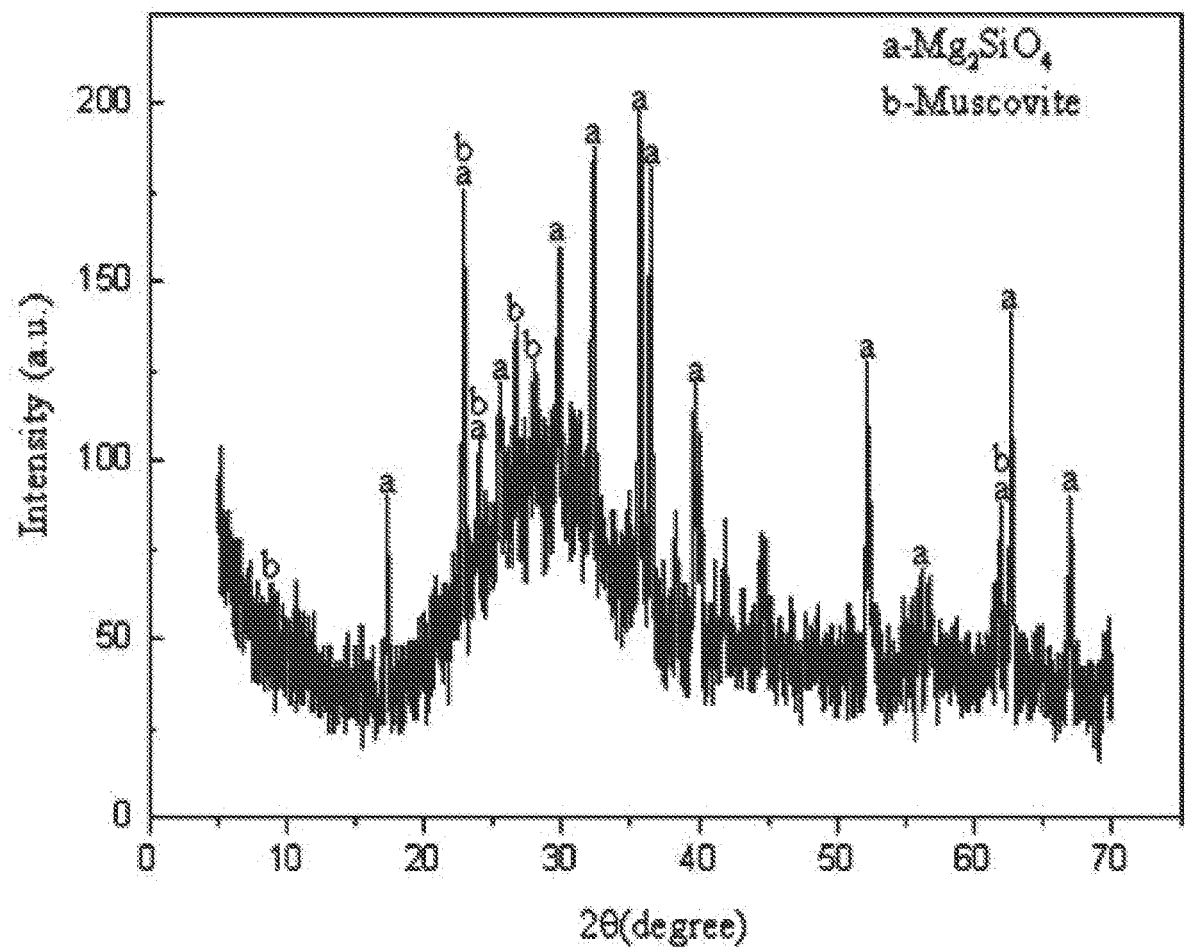

ADDITIVE FOR INCREASING EARLY ACTIVITY INDEX OF NICKEL SLAG AND PREPARATION METHOD THEREOF

CROSS REFERENCE TO RELATED APPLICATIONS

Applicant claims priority under 35 U.S.C. § 119 of Chinese Application No. 201910416728.5 filed on May 17, 2019, the disclosure of which is incorporated by reference.

TECHNICAL FIELD

The present invention relates to an additive for increasing an early activity index of nickel slag and a preparation method thereof, and belongs to the field of additive technologies.

BACKGROUND

Nickel slag is waste residue formed during metal nickel smelting. It is mainly composed of $SiO_2$, FeO, MgO, and CaO and contains different valuable metals such as nickel, iron, and cobalt. Due to different ore sources and smelting processes, chemical components and mineral compositions of nickel slag are extremely complex. Therefore, the nickel slag has not been well recycled. Currently, the utilization of nickel slag produced in the industry in China is relatively low. Most of nickel slag is directly stockpiled in a form of solid waste residue or treated by underground backfill, but this will result in land and water pollution.

Nickel slag contains $SiO_2$, FeO, $Fe_2O_3$, etc. Therefore, it can be added to a cement system as a supplementary cementing material to serve as an admixture. The nickel slag has extremely high content of glass phase. Under the activation of an alkaline medium, the nickel slag has specific hydration activity, Si—O and Al—O bonds on the surface of the vitreous body of the nickel slag can be easily broken, and the degree of polymerization of Si—O—Al network polymer is reduced. Therefore, the nickel slag can easily form a cementing product with a solution, so as to improve the strength of the consolidating body. Due to different components of nickel slag, various cementing components have quite different hydration and hardening characteristics and relatively low hydration activity.

In the cement concrete field, additives are commonly used to increase the hydration activity of a cementing material. However, there was little research on additives specially used for increasing an activity index of nickel slag. Nickel slag contains an alkaline medium, but the content of the alkaline medium is relatively low. Therefore, a hydration reaction of the nickel slag is relatively weak, and it is difficult to activate the hydration activity of the nickel slag. In the present invention, a hydration reaction is conducted by using an additive to improve the alkaline strength, thereby leading to secondary activation on nickel slag.

SUMMARY

A technical problem to be resolved in the present invention is to provide an additive for increasing an early activity index of nickel slag and a preparation method thereof.

To resolve the foregoing technical problem, the present invention provides an additive prepared through two-step synthesis of triethanolamine, maleic anhydride, and liquid bromine.

The present invention further includes a preparation method of an additive for increasing an early activity index of nickel slag, including the following steps: successively adding maleic anhydride and triethanolamine to a reactor; setting the heating temperature to 50° C. for reaction, where a large amount of heat is released during the reaction; when the reaction temperature decreases to 60° C. after heat is released in the reaction, allowing triethanolamine maleate to react with a solution of bromine in carbon tetrachloride; adding water to the mixture, where the weight percentage content of the added water is 60%; separating and removing carbon tetrachloride from water; and conducting uniform stirring to obtain the additive. A molar ratio of the maleic anhydride, the triethanolamine, and bromine is (0.2-1):1:(0.2-1), and a molar ratio of the maleic anhydride to the bromine is 1:1.

The introduction of ester groups, a hydroxy group, and a bromine group in a molecular formula of the additive prepared in the present invention facilitates improvement of the cement strength. Triethanolamine is weakly alkaline and is an alkali activator, and can reduce surface tension and an electric potential of a system. Moreover, triethanolamine has a catalytic effect, and can promote mineral dissolution and accelerate the formation of ettringite and calcium silicate hydrate. After the reaction between triethanolamine and maleic anhydride is conducted, ester groups and a hydroxy group are introduced. A reaction product contains a hydroxyl chain with specific steric hindrance. Polar functional groups such as the hydroxyl group have very strong hydrophilicity, and can be adsorbed on the surface of cement particles, thereby causing a hydration reaction and generating a large amount of hydration products. In this way, the cement compactness is improved, so as to improve the cement strength. The ester groups are easily bonded with calcium ions in cement, and can accelerate hydration of minerals such as tricalcium silicate and dicalcium silicate and improve the cement strength. Through an addition reaction between triethanolamine maleate and bromine, carbon-carbon double bonds in the triethanolamine maleate can be removed.

According to the foregoing technical solution, the present invention achieves the following technical effects:

According to the additive prepared in the present invention, based on triethanolamine, polar functional groups such as ester groups and a hydroxy group are introduced in triethanolamine maleate prepared by an esterification reaction. In this way, mineral dissolution can be promoted, and the formation of ettringite and calcium silicate hydrate can be accelerated. Calcium hydroxide is continuously produced as hydration proceeds, thereby activating the hydration activity of nickel slag and increasing an activity index of the nickel slag. When a dosage of the additive prepared in the present invention is 0.02% of the mass of the nickel slag, a 7 d activity index of the nickel slag can be increased by 22%-29%.

BRIEF DESCRIPTION OF DRAWINGS

The FIGURE is an XRD pattern of components of nickel slag.

DETAILED DESCRIPTION

To further elaborate the technical means for achieving the intended objective and effects thereof in the present invention, detailed description about the present invention is further provided below with reference to embodiments and application cases, but this is not intended to limit the present invention.

Embodiment 1

1 mol of triethanolamine and 0.2 mol of maleic anhydride were added to a reactor; the heating temperature was set to 50° C.; when the reaction temperature decreases to 60° C. after a large amount of heat is released in the reaction, triethanolamine maleate was allowed to react with 0.2 mol of a solution of bromine in carbon tetrachloride; water (with the weight percentage content of 60%) was added to the mixture; carbon tetrachloride was separated from water; and the obtained solution was uniformly stirred.

Embodiment 2

1 mol of triethanolamine and 0.4 mol of maleic anhydride were added to a reactor; the heating temperature was set to 50° C.; when the reaction temperature decreases to 60° C. after a large amount of heat is released in the reaction, triethanolamine maleate was allowed to react with 0.4 mol of a solution of bromine in carbon tetrachloride; water (with the weight percentage content of 60%) was added to the mixture; carbon tetrachloride was separated from water; and the obtained solution was uniformly stirred.

Embodiment 3

1 mol of triethanolamine and 0.6 mol of maleic anhydride were added to a reactor; the heating temperature was set to 50° C.; when the reaction temperature decreases to 60° C. after a large amount of heat is released in the reaction, triethanolamine maleate was allowed to react with 0.6 mol of a solution of bromine in carbon tetrachloride; water (with the weight percentage content of 60%) was added to the mixture; carbon tetrachloride was separated from water; and the obtained solution was uniformly stirred.

Embodiment 4

1 mol of triethanolamine and 0.8 mol of maleic anhydride were added to a reactor; the heating temperature was set to 50° C.; when the reaction temperature decreases to 60° C. after a large amount of heat is released in the reaction, triethanolamine maleate was allowed to react with 0.8 mol of a solution of bromine in carbon tetrachloride; water accounting for 60% of the mass of the total system was added to the mixture; carbon tetrachloride was separated from water; and the obtained solution was uniformly stirred.

Embodiment 5

1 mol of triethanolamine and 1 mol of maleic anhydride were added to a reactor; the heating temperature was set to 50° C.; when the reaction temperature decreases to 60° C. after a large amount of heat is released in the reaction, triethanolamine maleate was allowed to react with 1 mol of a solution of bromine in carbon tetrachloride; water (with the weight percentage content of 60%) was added to the mixture; carbon tetrachloride was separated from water; and the obtained solution was uniformly stirred.

Embodiment 6

Components of nickel slag selected for use are shown in the FIGURE. To determine an effect of the present invention, a nickel slag-containing cement base was prepared, and the additives prepared in Embodiments 1, 2, 3, 4, and 5 were separately added. According to the national standard for strength test for cement mortar and GB/T 12957-2005 "Test method for activity of industrial waste slag used as addition to cement", a dosage of the nickel slag was 30% of the mass of cement clinker, and a dosage of each of the additives prepared in the present invention was 0.02% of the mass of the nickel slag. After seven days of standard curing, the strength of the nickel slag-containing cement base was tested and activity indexes thereof were calculated. Obtained results are shown in Table 1:

Components of nickel slag selected for use are shown in the FIGURE. Obtained results of activity indexes of the slag are shown in Table 1:

TABLE 1

Results (wt %) of the impact of the additives prepared in the present invention on activity indexes of the nickel slag

| Additive | Dosage | Early activity (7 d) | Increased quantity of early activity (7 d) |
|---|---|---|---|
| None | — | 47 | — |
| Embodiment 1 | 0.02 | 71 | 24 |
| Embodiment 2 | 0.02 | 73 | 26 |
| Embodiment 3 | 0.02 | 75 | 25 |
| Embodiment 4 | 0.02 | 76 | 29 |
| Embodiment 5 | 0.02 | 69 | 22 |

It can be seen from Table 1, the additives prepared in Embodiments 1, 2, 3, 4, and 5 all increase a 7 d activity index of the nickel slag, among which the 7 d activity index can be increased by a maximum of 29%. Triethanolamine maleate can obviously affect an early activity index of the nickel slag, and effectively activate the hydration activity of the nickel slag.

What is claimed is:

1. A preparation method of an additive for increasing an early activity index of nickel slag, comprising the following steps:

successively adding maleic anhydride and triethanolamine to a reactor;

setting a heating temperature to 50° C. for reaction, wherein a large amount of heat is released during the reaction;

when the reaction temperature decreases to 60° C. after heat is released in the reaction, allowing triethanolamine maleate to react with a solution of bromine in carbon tetrachloride;

adding water to the mixture, wherein the weight percentage content of the added water is 60%;

separating and removing carbon tetrachloride from water; and conducting uniform stirring to obtain the additive, wherein a molar ratio of the maleic anhydride, the triethanolamine, and bromine is (0.2-1):1:(0.2-1), and a molar ratio of the maleic anhydride to the bromine is 1:1.

2. The preparation method according to claim 1, wherein the molar ratio of the maleic anhydride, the triethanolamine, and the bromine is 0.8:1:0.8.

3. An additive prepared by using the preparation method according to claim 1.

4. An additive prepared by using the preparation method according to claim 2.

* * * * *